(12) United States Patent
Chang et al.

(10) Patent No.: US 6,410,800 B1
(45) Date of Patent: Jun. 25, 2002

(54) PROCESS FOR PREPARING ACROLEIN

(75) Inventors: Tae Sun Chang; Deug Hee Cho; Dong Koo Lee, all of Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/671,999

(22) Filed: Sep. 29, 2000

(30) Foreign Application Priority Data

Sep. 30, 1999 (KR) .............................................. 99-41981

(51) Int. Cl.⁷ .............................................. C07C 45/35
(52) U.S. Cl. ........................ 568/479; 568/476; 568/480
(58) Field of Search ................................ 568/449, 476, 568/478, 479, 480

(56) References Cited

U.S. PATENT DOCUMENTS

| 4,732,884 A | * | 3/1988 | Sarumaru et al. ............ 502/205 |
| 5,700,752 A | * | 12/1997 | Kurimoto et al. ........... 502/311 |

FOREIGN PATENT DOCUMENTS

| KR | 0247556 | | 12/1999 |
| WO | 9941012 | * | 8/1999 |

* cited by examiner

*Primary Examiner*—Sreeni Padmanabhan
(74) *Attorney, Agent, or Firm*—Finnegan, Henderson, Farabow, Garrett & Dunner, L.L.P.

(57) ABSTRACT

The present invention relates to a process for preparing acrolein by the oxidation of propylene and more particularly, to the process for preparing acrolein in the presence of a solid catalyst having core-shell structure represented in the formula 1, $$[Bi_nA_aO_x][(100-z)\%E_eFe_1Ni_gMo_mO_y+z\%SiO_2] \qquad (1)$$

wherein A is at least one element selected from the group consisting of boron, phosphorus, and molybdenum;

E is at least one element having the atomic valence of 2;

when m is 1, n is 0.001–3, a is 0–3, e is 0–3, f is 0.01–5, g is 0.1–5, and z is 0–90; and x and y are numbers such that the valence requirements of the other elements for Oxygen in the core and shell catalytic phase, respectively, are satisfied.

2 Claims, No Drawings

PROCESS FOR PREPARING ACROLEIN

BACKGROUND OF THE INVENTION

1. Field of the Invention

The present invention relates to a process for preparing acrolein by the oxidation of propylene and more particularly, to the process for preparing acrolein in the presence of a solid catalyst having a core-shell structure represented in the formula 1, $$[Bi_nA_aO_x][(100-z)\%E_eFe_fNi_gMo_mO_y+z\%SiO_2] \quad (1)$$

wherein A is at least one element selected from the group consisting of boron, phosphorus, and molybdenum;
E is at least one element having the atomic valence of 2;
when m is 1, n is 0.001–3, a is 0–3, e is 0–3, f is 0.01–5, g is 0.1–5, and z is 0–90; and
x and y are numbers such that the valence requirements of the other elements for oxygen in the core and shell catalytic phase, respectively, are satisfied.

2. Description of the Prior Art

Acrolein has been widely used as a raw material in the synthesis of acylates and fine chemical products such as fibers, papers, paints, adhesives, and leathers. Further, demand of acrolein is continuously increased with the development of polymer related technologies and there are also trending to develop applications thereof in various fields.

Acrolein has been first synthesized by high temperature degradation of glycerin and further vapor-phase oxidation of acrolein gives acrylic acid. Since after, acetylene method using Ni as a catalyst, ethylene method using Pd as a catalyst, hydrolysis of acrylonitrile by using sulfuric acid and the like have been developed to synthesize acrolein. The most industrially useful and attractive method is by the oxidation of propylene due to its economic merit. On the other hand, the aldol condensation of formaldehyde and acetic acid has been extensively studied.

General process for preparing acrolein is by the oxidation of propylene in the presence of a mixed oxide catalyst having Bi—Mo—O system at about 400° C. And further oxidation of acrolein is performed at about 300° C. in the presence of an oxide catalyst having Mo—V—O system to produce acrylic acid.

In Korea, I.G company has introduced Nippon Shokubai process to prepare acrolein and acrylic acid and this process is divided into two stages. The first stage of process is to produce acrolein in the presence of a mixed oxide catalyst having Bi—Mo—Fe—Co—O system at a reaction temperature of 325° C. and a pressure of 2.5–3.0 atm and the second is to produce acrylic acid in the presence of a molybdate oxide catalyst at a reaction temperature of 270° C. and a pressure of 2 atm. Total yield of the process to produce acrolein and acrylic acid is 81 to 85%.

Use of a catalyst in the oxidation of olefins brought an importance of selection of a catalyst, and results in extensive studies relating to such catalysts. Further, it has been developed not only in processes of reactions but also in compositions of catalyst and processes for preparing thereof. As a result, yield of producing acrylic acid by the oxidation is over 90%, and yield of producing acrylonitrile by ammoxidation is over 80% in plant.

Korean Patent No. 0247556, which is registered by the inventors of the present invention, discloses the use of a solid catalyst having core-shell structure in the preparation of acrylonitrile by ammoxidation of olefins. They have proved that said solid catalyst comprising a core catalyst phase containing Mo, Fe, Ni, and Si which is prepared by slurry technique, and a shell catalyst phase containing bismuth which is prepared by a impregnation technique using the core catalyst phase as a support, provides more excellent activities than conventional catalysts by examining their activities.

SUMMARY OF THE INVENTION

The present invention has been accomplished by obtaining the fact that use of the solid catalyst having a core-shell structure disclosed in Korea Patent No. 0247556 exhibits excellent activity in the oxidation of propylene to give acrolein.

Therefore, an object of the present invention is to provide a process for preparing acrolein at a high yield.

DETAILED DESCRIPTION OF THE INVENTION

The present invention relates to a process for preparing acrolein by the oxidation of propylene and more particularly, to the process for preparing acrolein in the presence of a solid catalyst having core-shell structure represented in the formula 1, $$[Bi_nA_aO_x][(100-z)\%E_eFe_fNi_gMo_mO_y+z\%SiO_2] \quad (1)$$

wherein A is at least one element selected from the group consisting of boron, phosphorus, and molybdenum;
E is at least one element having the atomic valence of 2;
when m is 1, n is 0.001–3, a is 0–3, e is 0–3, f is 0.01–5, g is 0.1–5, and z is 0–90; and
x and y are numbers such that the valence requirements of the other elements for oxygen in the core and shell catalytic phase, respectively, are satisfied.

The Detailed description of the present invention is given hereunder.

The present invention is characterized by use of a solid catalyst having a core-shell structure for preparing acrolein from propylene by the oxidation at a high yield.

According to Korea Patent No. 0247556, the activities of such a catalyst having the core-shell structure vary with compositions and ratios of each component comprised in the core phase and the shell phase, even the chemical composition of the catalyst is the same. The maximum activity of the solid catalyst is achieved when the core phase comprises $[(100-z)\%E_eFe_fNi_gMo_mO_y+z\%SiO_2]$ and the shell phase comprises $[Bi_nA_aO_x]$ by the synergy effect. Further, it affects manufacturing cost by using minimum content of expensive bismuth which is an essential component of the conventional catalyst.

This present invention is also characterized by a process for preparing acrolein at a high yield by the oxidation of propylene in the presence of said solid catalyst having a core-shell structure, and the oxidation condition is described in detail.

The reaction temperature of oxidation is in the range of 300 to 500° C., preferably 350 to 400° C. If the reaction temperature deviates from the range, it causes such problems in the conversion of propylene and selectivity to acrolein due to increase of un-reacted reactants or by-products. Preferred pressure of the reaction is in the range of 1 to 5 atm. If the pressure deviates from the range, the selectivity to / rapidly decreases. The reaction can be affected by the ratio of reactants. Preferred molar ratio of reactants (propylene/oxygen/nitrogen) is 1/1 to 20/1 to 20. The reaction can be also affected by the contact time and preferred contact time is in the range of 0.5 to 5 seconds.

The mechanism of the oxidation of propylene in the presence of the solid catalyst having a core-shell structure is described in detail hereunder.

In the catalyst having a core-shell structure, the core and shell catalytic phase functions independently and differently and the activity of the catalyst varies with the composition thereof and the ratio of each component comprised therein. According to the present invention, when the core phase comprises $[(100-z)\%E_eFe_fNi_gMo_mO_y+z\%SiO_2]$ and the shell phase comprises $[Bi_nA_aO_x]$, the maximum activity of the solid catalyst is achieved by the synergy effect.

The following examples illustrate various aspects of this invention but are not to be construed to limit the claims in any manner whatsoever.

COMPARATIVE EXAMPLES 1 TO 4

Solution A was prepared by dissolving 18.66 g of $Fe(NO_3)_3 \cdot 9H_2O$, and 39.33 g of $Ni(NO_3)_2 \cdot 6H_2O$ in 150 ml of 10% $HNO_3$ solution containing $Bi(NO_3)_3 \cdot 5H_2O$ with the amount represented in the following table 1. Solution B was prepared in such a manner that after 29.12 g of $(NH_4)_6Mo_7O_{24} \cdot 4H_2O$ was dissolved in 240 ml of water by heating, 93.83 g of 40% silica sol and $H_3PO_4$ with the amount represented in the following table 1 were added to the mixture. After mixing Solution A with solution B, pH of the resulting mixture was adjusted to 3. After evaporating the solvent of the resulting mixture by heating on a hot plate, the residue was dried in oven at 140° C., and calcined to obtain a desired catalyst.

COMPARATIVE EXAMPLES 5 TO 9 AND EXAMPLES 1 TO 9

Solution A was prepared by dissolving 18.66 g of $Fe(NO_3)_3 \cdot 9H_2O$, and 39.33 g of $Ni(NO_3)_2 \cdot 6H_2O$ in 150 ml of 10% $HNO_3$ solution. Solution B was prepared in such a manner that after 29.12 g of $(NH_4)_6Mo_7O_{24} \cdot 4H_2O$ was dissolved in 240 ml of water by heating, 93.83 g of 40% silica sol was added to the mixture. After mixing Solution A with solution B, $Bi(NO_3)_3 \cdot 5H_2O$ and $H_3PO_4$ with the amount represented in the following table 1 were added into the mixture and pH of the resulting mixture was adjusted to 3. After evaporating the solvent of the resulting mixture by heating on a hot plate, the residue was dried in oven at 140° C., and calcined to obtain a desired catalyst.

TABLE 1

| Category | | Catalyst composition |
|---|---|---|
| Comparative Example | 1 | $[50\% \, MoFe_{0.28}Ni_{0.82}O_y + 50\% \, SiO_2]$ |
| | 2 | $[50\% \, MoFe_{0.28}Ni_{0.82}O_y + 50\% \, SiO_2]$ |
| | 3 | $[50\% \, MoFe_{0.28}Ni_{0.82}O_y + 50\% \, SiO_2]$ |
| | 4 | $[Bi_{0.03}MoFe_{0.28}Ni_{0.82}O_y + 50\% \, SiO_2]$ |
| | 5 | $[Bi_{0.03}P_{0.03}MoFe_{0.28}Ni_{0.82}O_y + 50\% \, SiO_2]$ |
| | 6 | $[Bi_{0.01}P_{0.01}MoFe_{0.28}Ni_{0.82}O_y + 50\% \, SiO_2]$ |
| | 7 | $[Bi_{0.03}P_{0.03}O_x][50\% \, MoFe_{0.28}Ni_{0.82}O_y + 50\% \, SiO_2]$ |
| | 8 | $[Bi_{0.03}P_{0.03}O_x][50\% \, MoFe_{0.28}Ni_{0.82}O_y + 50\% \, SiO_2]$ |
| | 9 | $[Bi_{0.03}P_{0.03}O_x][50\% \, MoFe_{0.28}Ni_{0.82}O_y + 50\% \, SiO_2]$ |
| | 10 | $[Bi_{0.03}P_{0.03}O_x][50\% \, MoFe_{0.28}Ni_{0.82}O_y + 50\% \, SiO_2]$ |
| | 11 | $[Bi_{1.0}O_x][50\% \, MoFe_{0.28}Ni_{0.82}O_y + 50\% \, SiO_2]$ |
| Example | 1 | $[Bi_{0.03}P_{0.03}O_x][50\% \, MoFe_{0.28}Ni_{0.82}O_y + 50\% \, SiO_2]$ |
| | 2 | $[Bi_{0.02}O_x][50\% \, MoFe_{0.28}Ni_{0.82}O_y + 50\% \, SiO_2]$ |
| | 3 | $[Bi_{0.03}O_x][50\% \, MoFe_{0.28}Ni_{0.82}O_y + 50\% \, SiO_2]$ |
| | 4 | $[Bi_{0.03}P_{0.03}O_x][50\% \, MoFe_{0.28}Ni_{0.66}Co_{0.16}O_y + 50\% \, SiO_2]$ |
| | 5 | $[Bi_{0.03}P_{0.03}O_x][50\% \, MoFe_{0.28}Ni_{0.69}Mn_{0.13}O_y + 50\% \, SiO_2]$ |
| | 6 | $[Bi_{0.03}P_{0.03}O_x][50\% \, MoFe_{0.28}Ni_{0.66}Mg_{0.16}O_y + 50\% \, SiO_2]$ |
| | 7 | $[Bi_{0.03}P_{0.03}O_x][50\% \, MoFe_{0.28}Ni_{0.69}Co_{0.06}O_y + 50\% \, SiO_2]$ |
| | 8 | $[Bi_{0.03}P_{0.03}O_x][50\% \, MoFe_{0.28}Ni_{0.69}Mn_{0.07}Co_{0.06}O_y + 50\% \, SiO_2]$ |
| | 9 | $[Bi_{0.03}P_{0.03}O_x][50\% \, MoFe_{0.28}Ni_{0.69}Mn_{0.07}Co_{0.06}O_y + 50\% \, SiO_2]$ |

The oxidation of propylene in the presence of obtained catalyst represented in table 1 was performed by the reaction condition represented in the following table 2. The conversion of propylene and selectivity to acrolein were determined and described in the table 2. Such reactivity was determined by gas chromatography equipped with flame ionization detector and thermal conductivity detector to detect the selectivity toward carbon dioxide, carbon monoxide, methane, ethane, ethylene and the like. The conversion of propylene and the selectivity to acrolein were defined as follows;

1) The conversion of propylene (moles of reactant reacted)/(moles of total reactant)

2) Selectivity to acrolein (moles of product produced)/(moles of reactant reacted).

TABLE 2

| Category | Reaction condition | | | | Reactivity | |
| --- | --- | --- | --- | --- | --- | --- |
| | Temp. (° C.) | Pressure (atm) | Molar ratio (propylene/oxygen/nitrogen) | Contact time (sec) | Conversion (%) | Selectivity to acrolein (%) |
| Comparative example | | | | | | |
| 1 | 360 | 1 | 1/3/14 | 0.6 | 8.2 | 32.8 |
| 2 | 360 | 1 | 1/3/14 | 0.6 | 62.5 | 89.2 |
| 3 | 360 | 1 | 1/3/14 | 0.6 | 62.5 | 87.6 |
| 4 | 360 | 1 | 1/3/14 | 0.6 | 62.0 | 90.8 |
| 5 | 410 | 1 | 1/3/14 | 0.6 | 59.0 | 30.7 |
| 6 | 360 | 1.2 | 1/3/14 | 0.6 | 65.4 | 71.3 |
| 7 | 360 | 1 | 1/9/14 | 0.6 | 63.9 | 79.8 |
| 8 | 360 | 1 | 1/3/14 | 1.2 | 71.2 | 65.5 |
| 9 | 360 | 1 | 1/3/14 | 0.6 | 50.2 | 63.0 |
| Example | | | | | | |
| 1 | 360 | 1 | 1/3/14 | 0.6 | 75.9 | 90.7 |
| 2 | 360 | 1 | 1/3/14 | 1.2 | 78.0 | 89.5 |
| 3 | 360 | 1 | 1/3/14 | 1.8 | 87.3 | 96.5 |
| 4 | 360 | 1 | 1/3/14 | 0.6 | 79.7 | 83.9 |
| 5 | 360 | 1 | 1/3/14 | 0.6 | 77.6 | 82.4 |
| 6 | 360 | 1 | 1/3/14 | 0.6 | 78.2 | 88.7 |
| 7 | 360 | 1 | 1/3/14 | 0.6 | 80.4 | 87.9 |
| 8 | 360 | 1 | 1/3/14 | 0.6 | 81.2 | 85.8 |
| 9 | 360 | 1 | 1/3/14 | 0.6 | 74.6 | 88.9 |
| 10 | 360 | 1 | 1/3/14 | 1.2 | 85.6 | 95.0 |
| 11 | 360 | 1 | 1/3/14 | 1.8 | 96.1 | 95.8 |

As described above, the solid catalysts represented in formula 1 having the core-shell structure prepared in Examples 1 to 11 exhibit superior activity to those prepared by Comparative Examples 1 to 9. Further, the solid catalyst of the present invention is more attractive because of the significant price difference for minimum using of expensive bismuth. The fact can be compared example 3 to comparative example 9. Therefore, the process of the present invention is preferable to produce acrolein industrially.

What is claimed is:

1. A process for preparing acrolein in the presence of a solid catalyst having a core-shell structure represented in formula 1 by the oxidation of propylene, $$[Bi_nA_aO_x][(100-z)\%E_eFe_fNi_gMo_mO_y + z\%SiO_2] \quad (1)$$

wherein A is at least one element selected from the group consisting of boron, phosphorus, and molybdenum;

E is at least one element having the atomic valence of 2;

when m is 1, n is 0.001–3, a is 0–3, e is 0–3, f is 0.01–5, g is 0.1–5, and z is 0–90; and x and y are numbers such that the valence requirements of the other elements for Oxygen in the core and shell catalytic phase, respectively, are satisfied.

2. The process for preparing acrolein according to claim 1, wherein said oxidation reaction is performed under following condition: a temperature of 300 to 500° C.; a pressure of 1 to 5 atm; a volume ratio of reactants, propylene/oxygen/nitrogen, of 1/(1 to 20)/(1 to 20); and a contact time of 0.5 to 5 seconds.

* * * * *